(12) United States Patent
Ishitani et al.

(10) Patent No.: US 6,521,890 B2
(45) Date of Patent: *Feb. 18, 2003

(54) FOCUSED ION BEAM MACHINING METHOD AND FOCUSED ION BEAM MACHINING APPARATUS

(75) Inventors: Tohru Ishitani, Sayama (JP); Tsuyoshi Ohnishi, Hitachinaka (JP); Megumi Aizawa, Hitachi (JP); Hiroji Iwata, Hitachinaka (JP)

(73) Assignee: Hitachi, Ltd., Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/346,204

(22) Filed: Jul. 1, 1999

(65) Prior Publication Data

US 2002/0092985 A1 Jul. 18, 2002

(30) Foreign Application Priority Data

Jul. 3, 1998 (JP) .......................................... 10-188969

(51) Int. Cl.$^7$ ............................................. H01J 37/304
(52) U.S. Cl. ...................................................... 250/309
(58) Field of Search ........................... 250/309, 492.21, 250/491.1

(56) References Cited

U.S. PATENT DOCUMENTS 5,656,811 A * 8/1997 Itoh et al. .................... 250/309
5,952,658 A * 9/1999 Shimase et al. ............ 250/309

FOREIGN PATENT DOCUMENTS

JP     9274879 A    10/1997
JP     9306402 A    11/1997

* cited by examiner

Primary Examiner—Kiet T. Nguyen
(74) Attorney, Agent, or Firm—Kenyon & Kenyon

(57) ABSTRACT

When SIM image data D[n] of a mark is compared with reference SIM image data in calculating a displacement of machining position in the nth time, image data D[n−1] just before the nth time is employed as the reference image data and a position displacement of the image is obtained from matching processing of the two kinds of image data of D[n] and D[n−1] to calculate a displacement of machining position.

8 Claims, 11 Drawing Sheets n=0 n=20 n=40 n=60

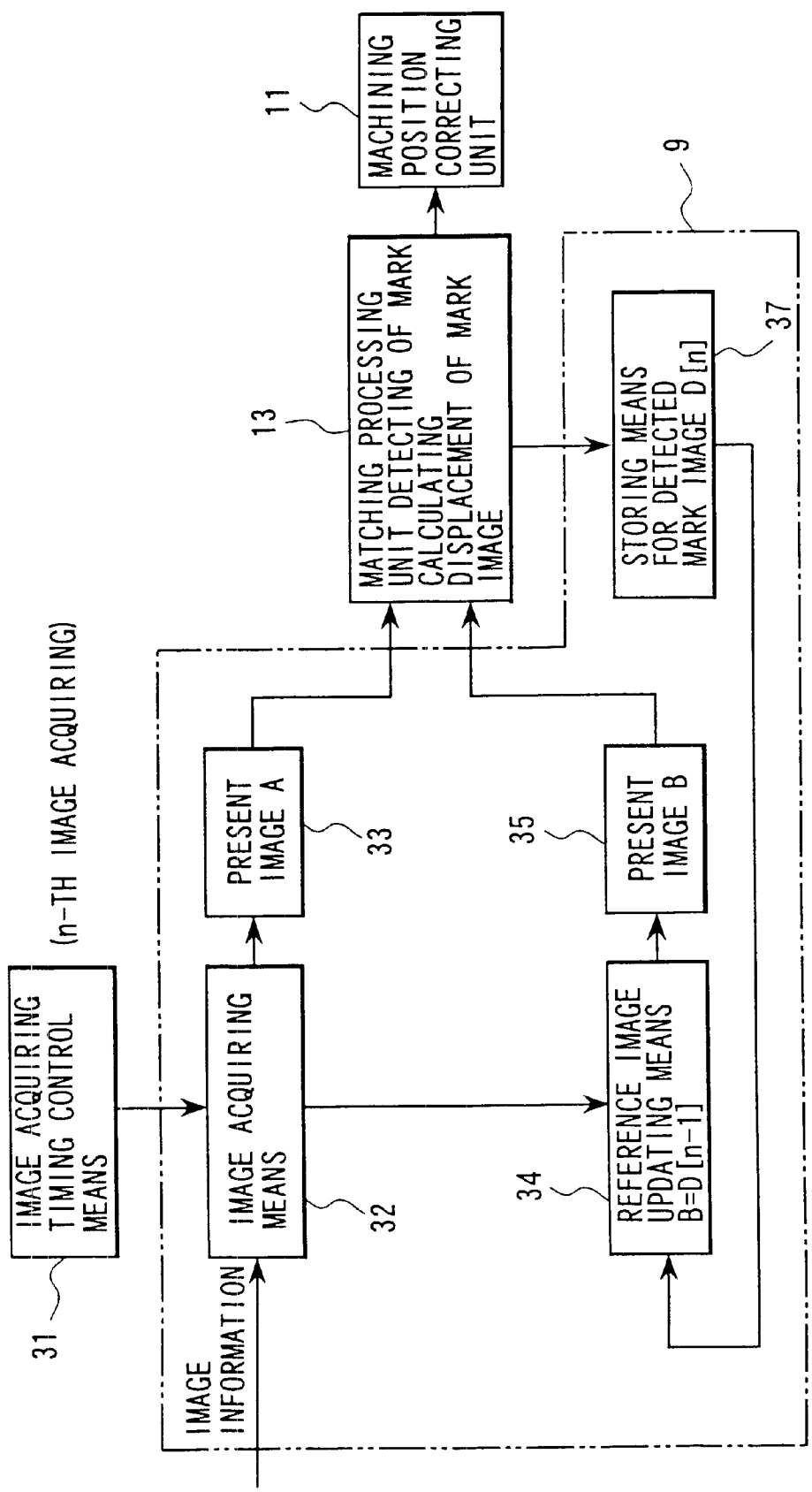

BEFORE MACHINING

DURING MACHINING 1

DURING MACHINING 2

FIG.10A
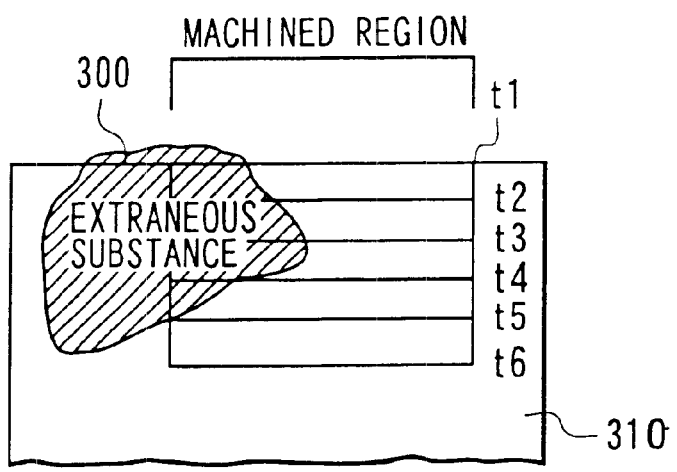
FIG.10B
(1) t1
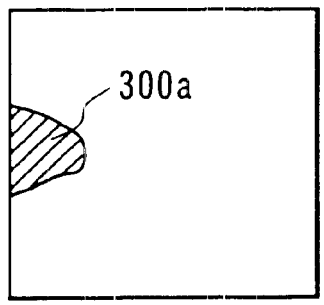
(2) t2
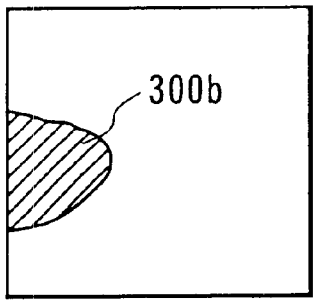
(3) t3
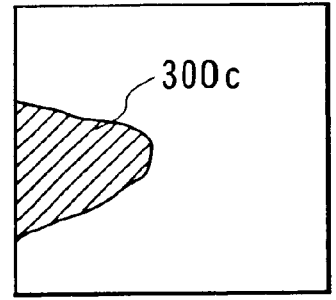
(4) t4
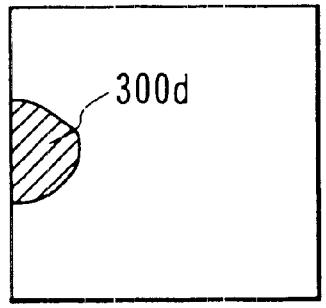
(5) t5
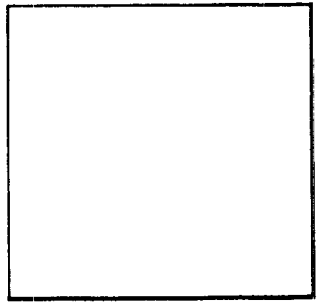
(6) t6
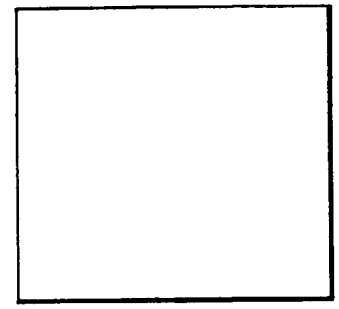

FOCUSED ION BEAM MACHINING METHOD AND FOCUSED ION BEAM MACHINING APPARATUS

BACKGROUND OF THE INVENTION

The present invention relates to a focused ion beam (hereinafter, referred to as an FIB) machining method and an FIB machining apparatus which are effective in micromachining using a focused ion beam such as cross-sectional machining of micro-devices or new functional materials, preparing of [the] samples for a transmission electron microscope (hereinafter, referred to as TEM), manufacturing of micromachine parts and, more particularly, to an FIB processing method and an FIB processing apparatus which correct a [position] displacement of a beam irradiation position during long-irradiation machining.

An FIB apparatus is disclosed, for example, in Japanese Patent Application Laid-Open No. 9-306402. A method of correcting a machining position is disclosed, for example, in Japanese Patent Application Laid-Open No. 9-274879.

FIG. 12 is a functional block diagram of a conventional FIB machining apparatus. In a vacuum enclosure of the FIB apparatus surrounded by a dashed line, an ion source unit 1 for emitting ions, an ion beam control system 2 for accelerating, focusing and deflecting an ion beam emitted from the ion source unit 1, a sample chamber unit 3 for loading and transporting a sample and a secondary particle detector 6 for detecting secondary electrons and secondary ions emitted from the sample are arranged. The ion beam control system 2 includes a condenser lens, an ion beam control aperture plate, an aligner stigmator, a blanker, a deflector and an objective lens. An ion source control unit 4 and an ion beam control unit 5 are connected to the ion source unit 1 and the ion beam control system 2, respectively. A computer unit 7 is connected to the ion source control unit 4 and the ion beam control unit 5 to control these units together. The computer unit 7 comprises an image control unit 9 for acquiring a scanning ion microscopic (hereinafter, referred to as an SIM) image based on an output signal of a secondary particle detector 6, the image control unit 9 being composed of an image memory and an image processing unit; a CRT 8 for displaying the SIM image; an input operation unit 10 such as a keyboard and a mouse; a mark detecting unit 12; and a machining position correcting unit 11.

In this conventional technology, correction of a displacement of a machining position is performed by the following means during long-time machining within a narrow region which is not required to move its sample stage. Initially, ①  a position of a mark for correcting a beam irradiation position selected prior to starting the machining is detected from an SIM image and registered. Then, ② a mark position is detected by acquiring the SIM image of the registered mark at preset intervals during machining, and a position displacement in beam irradiation position is calculated by comparing the detected position with the position of the registered mark to perform correction control of the displacement of the machining position.

In the above-mentioned conventional method, the mark position is repetitively detected by irradiating the FIB and acquiring the SIM image of the registered mark during machining. However, since the mark is eroded by an ion sputtering phenomenon during acquiring the SIM image, the mark is gradually deformed by the damage that occurs when the number of times of detecting the mark is increased. Therefore, there is a disadvantage in that when the mark deformation becomes too large to detect the mark, the displacement of the machining position can not accurately corrected.

SUMMARY OF THE INVENTION

The present invention solves such a problem in the conventional technology. An object of the present invention is to provide an FIB machining method and an FIB machining apparatus which can correct a displacement of machining position using a mark for detecting the displacement of machining position even if the mark is damaged by an ion sputtering phenomenon and the shape of the mark is largely changed from the shape of the mark registered prior to starting of the machining.

Further, another object of the present invention is to provide a novel method for automatically detecting termination of an FIB machining.

In order to attain the above objects, in the present invention, when the displacement of machining position in the nth time (where n=1, 2, 3, . . . ) is calculated, SIM image data $D[n-1]$ acquired in the time just before the nth time, that is, in the $(n-1)$th time is employed as the reference SIM image data. Then, a position displacement of the image is obtained from matching processing of the two kinds of SIM image data, $D[n]$ and $D[n-1]$, to calculate a displacement of machining position.

In the conventional technology, the reference SIM image data is always SIM image data $D[0]$ before starting of machining and is not updated. Therefore, if SIM image data $D[n]$ acquired in the nth time becomes significantly different from the SIM image data $D[0]$ before starting of machining, a large error is produced when matching processing of the two kinds of SIM image data, $D[n]$ and $D[0]$, is performed or, the matching processing can not be performed. In the present invention, since the SIM image data $D[n-1]$ acquired in the time just before the nth time is employed as the reference SIM image data to be compared with the SIN image data $D[n]$, a displacement of machining position can be accurately calculated every updating, even if the mark shape becomes significantly different from that in the initial period of the machining so long as an analogy between the two kinds of data of $D[n]$ and $D[n-1]$ is maintained.

Although the mark is typically set outside an FIB machining region of a sample, setting of the mark outside an FIB machining region of a sample is not absolutely necessary. It is possible to select a distinctive structure in an SIM image inside an FIB machining region and set it as a mark. In a case of a cross-sectional structure where the selected mark is buried in the sample, the machining can progress while the machining region is changed so as to trace the mark (structure) by correcting the FIB irradiation position based on the matching processing between the two kinds of SIM image data, $D[n]$ and $D[n-1]$.

Further, it is also possible to set a mark in an FIB machining region and use it for detecting a termination of the FIB machining. For example, in a case where the mark is part of a structural body in the sample and a section of the structural body is intended to be formed by FIB machining, the FIB machining is performed while the mark (structural body) appearing in the SIM image is being monitored, and the machining is stopped at the time when the mark disappears from the SIM image or when a preset time after disappearance of the mark has elapsed. Thus, a desired section can be formed.

That is, the present invention is characterized by a focused ion beam machining method of machining a sample using a focused ion beam, the method comprising the steps of acquiring a scanning ion microscopic image of the sample at preset time intervals; calculating a position displacement of the image based on image data D[n−1] in a specified region inside a scanning ion microscopic image in the (n−1)th time and image data D[n] in the specified region inside a scanning ion microscopic image in the nth time acquired in the above step, where n=1, 2, 3, . . . ; and correcting a machining position by displacing an irradiation position of the focused ion beam by the calculated position displacement.

The scanning ion microscopic image of the sample is displayed on an image display apparatus such as a CRT by scanning on the sample with the focused ion beam and by detecting intensity of secondary particles such as secondary electrons or secondary ions emitted from the sample in synchronism with the scanning.

The specified region for acquiring the image data D[n] inside the scanning ion microscopic image may be a region which is located outside a machined region and includes a distinctive pattern. The distinctive pattern located outside the machined region may be a mark pattern formed prior to starting of machining. Otherwise, the specified region inside the scanning ion microscopic image may be a region located inside a machined region and including a distinctive pattern.

The time interval between acquiring the scanning ion microscopic images may be shortened when the position displacement of the image is larger than a first set value, and the time interval between acquiring the scanning ion microscopic images may be lengthened when the position displacement of the image is smaller than a second set value.

Further, the present invention is characterized by a focused ion beam machining method of machining a sample using a focused ion beam, the method comprising the steps of acquiring a scanning ion microscopic image of a region containing a distinctive pattern located inside a machining region of the sample at preset time intervals; detecting a change in shape of the pattern based on image data D[n−1] in a specified region inside a scanning ion microscopic image in the (n−1)th time and image data D[n] in the specified region inside a scanning ion microscopic image in the nth time acquired in the above step, where n=1, 2, 3, . . . ; and judging that machining be terminated based on the shape change of the pattern. The shape change of the pattern includes disappearance of the pattern.

A focused ion beam machining apparatus in accordance with the present invention is characterized by a focused ion beam machining apparatus having an ion source, and an ion beam control system for accelerating, focusing and deflecting an ion beam emitted from the ion source, which further comprises a secondary particle detector for detecting secondary particles emitted from a sample by irradiating the ion beam onto the sample; an image control unit for acquiring a scanning ion microscopic image of the sample at preset time intervals based on an output of the secondary particle detector; a matching processing unit for calculating a position displacement of the image from matching processing of image data D[n−1] in a specified region inside a scanning ion microscopic image in the (n−1)th time and image data D[n] in the specified region inside a scanning ion microscopic image in the nth time, acquired by said image control unit, where n=1, 2, 3, . . . ; and a control unit for controlling the ion beam control system so as to compensate the position displacement of the image calculated by the matching processing unit.

Further, a focused ion beam machining apparatus in accordance with the present invention is characterized by a focused ion beam machining apparatus having an ion source, and an ion beam control system for accelerating, focusing and deflecting an ion beam emitted from the ion source, which further comprises a secondary particle detector for detecting secondary particles emitted from a sample by irradiating the ion beam onto the sample; an image control unit for acquiring a scanning ion microscopic image of the sample at preset time intervals based on an output of the secondary particle detector; and an image comparing unit for comparing image data D[n−1] in a specified region inside a scanning ion microscopic image in the (n−1)th time and image data D[n] in the specified region inside a scanning ion microscopic image in the nth time acquired by the image control unit, where n=1, 2, 3, . . . , wherein machining is terminated when a predetermined degree of matching between the two kinds of image data compared by the image comparing unit is reached.

According to the present invention, a displacement of machining position during long-time FIB machining can be corrected without involvement of an operator, which contributes to highly accurate machining positions and to semi-automatic machining. In regard to machining of a plurality of machining positions in a plurality of samples, the machining of all of them can be automatically and continuously performed over a several hour period, without involvement by an operator, by pre-registering these machining positions and machining conditions.

In addition, according to the present invention, since a termination of FIB machining can be automatically determined, the FIB machining apparatus can be automatically operated.

BRIEF DESCRIPTION OF DRAWINGS

FIG. 5 is a functional block diagram of the image control unit and the matching processing unit of FIG. 2;

FIG. 10A and

FIG. 10B are explanatory views showing a method capable of automatically determining termination of machining;

DESCRIPTION OF THE PREFERRED EMBODIMENTS

Embodiments of the present invention will be described below, referring to the accompanied drawings.

Figure 1:
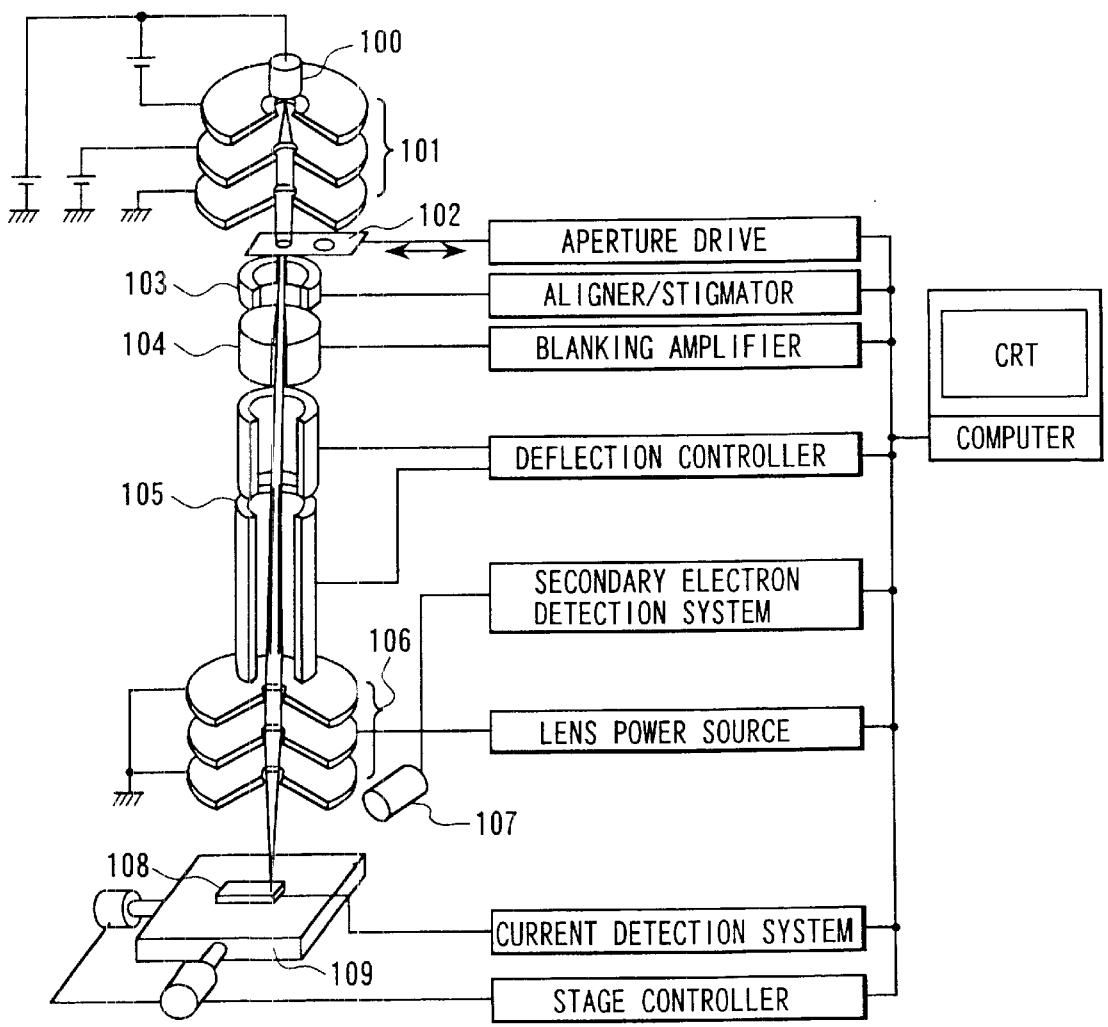
FIG. 1 is a schematic view showing an embodiment of an FIB apparatus in accordance with the present invention.

FIG. 1 is a schematic view showing an embodiment of an FIB apparatus in accordance with the present invention. An ion beam emitted from a metal ion source 100 is focused onto a sample 108 by a condenser lens 101 and an objective lens 106. An ion beam restricting aperture plate 102, an aligner/stigmator 103, a blanker 104 and a deflector 105 are arranged between the lenses. The sample 108 is mounted on a sample stage 109, and can be finely moved in an X- and Y-directions. The secondary particles emitted from the sample 108 such as secondary electrons and secondary ions are detected by a charged particle detector 107. Brightness modulation of an image display such as a CRT is performed with the intensity of a signal of the charged particle detector 107, and a SIM image of the sample surface is formed on the CRT by using a signal in synchronism with a beam deflection signal as a beam scanning signal.

Figure 2:
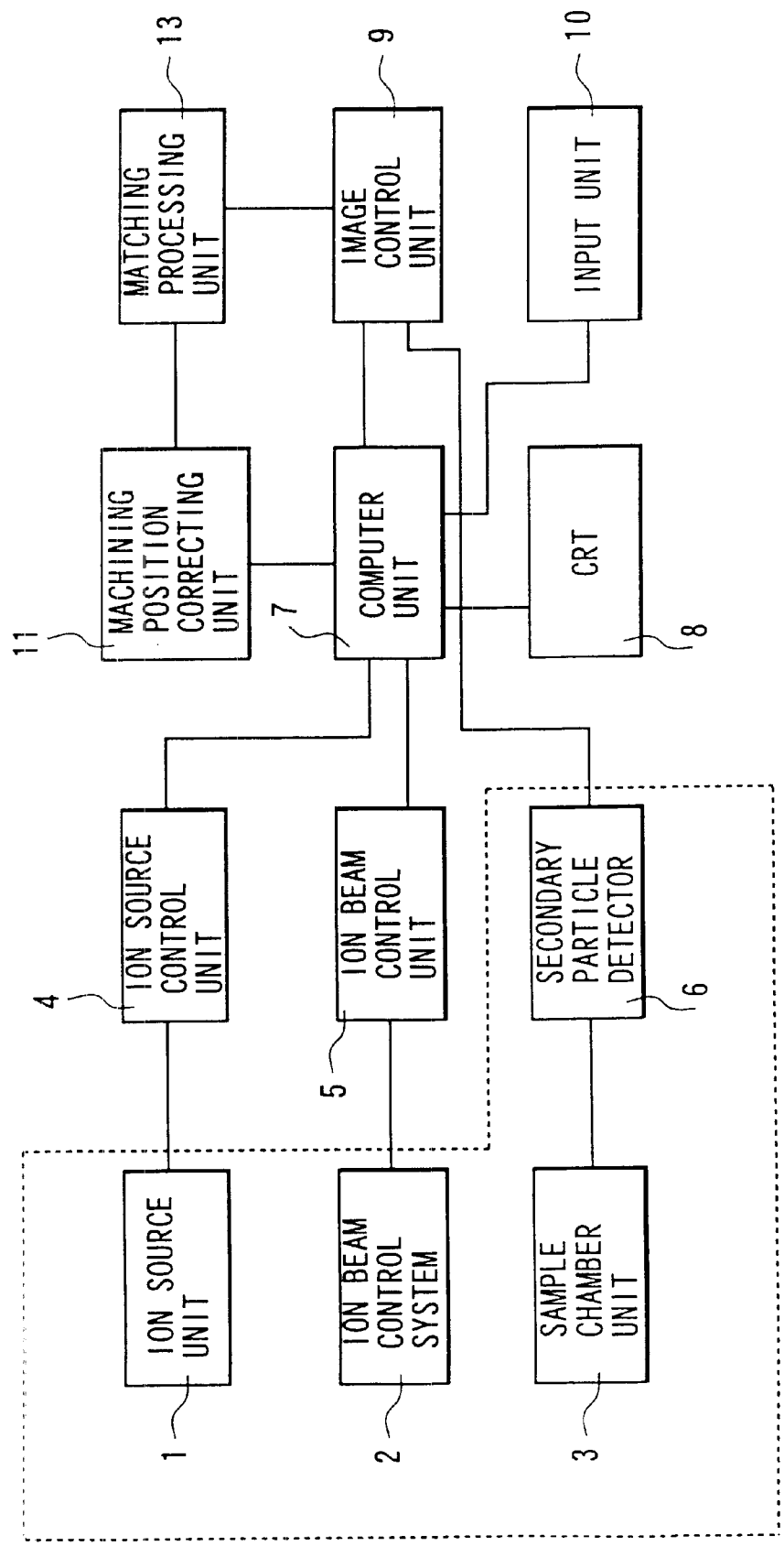
FIG. 2 is a functional block diagram of an FIB machining apparatus in accordance with the present invention.
Figure 12:
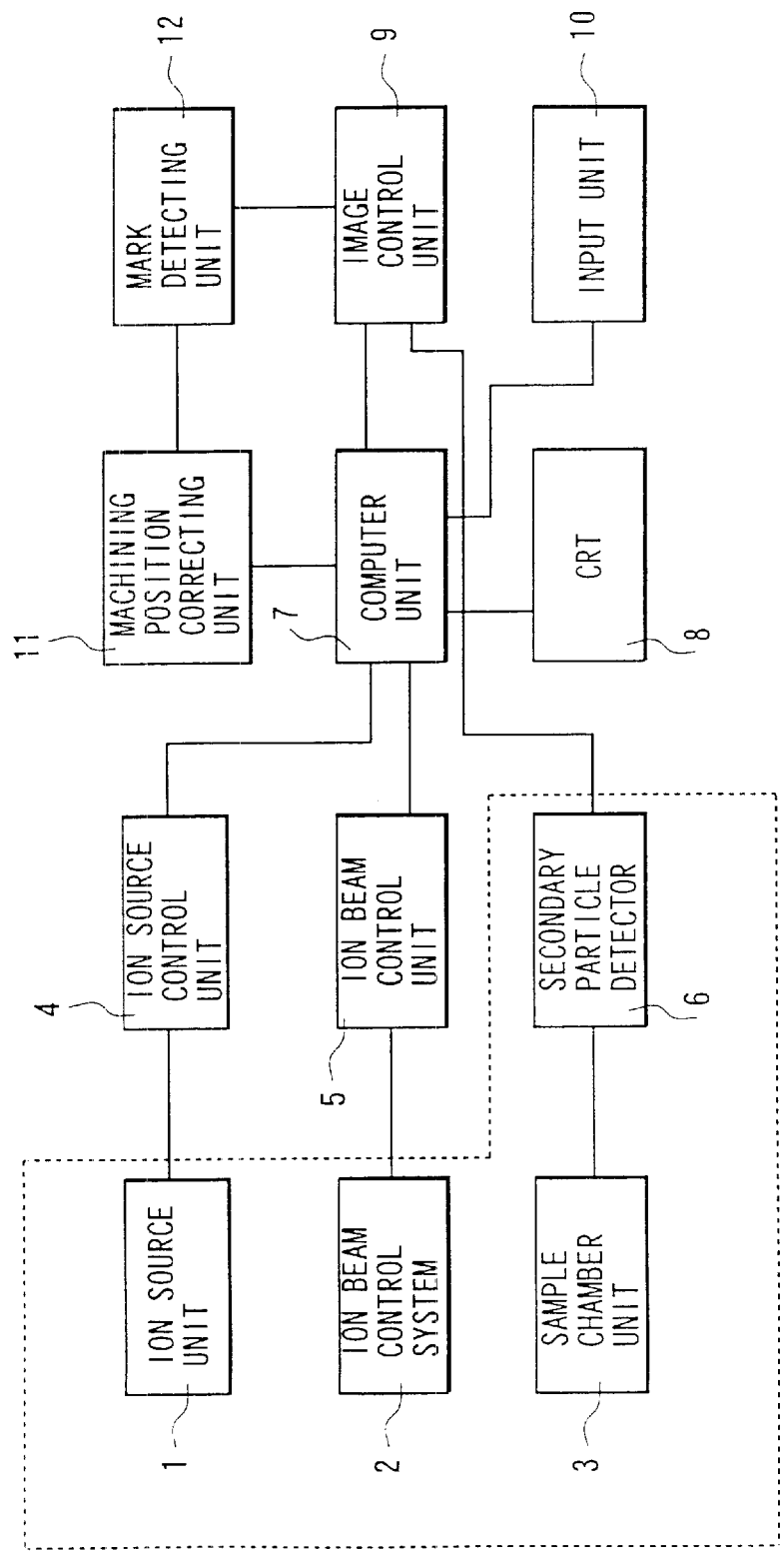
FIG. 12 is a functional block diagram of a conventional FIB machining apparatus.

FIG. 2 is a functional block diagram of an FIB machining apparatus in accordance with the present invention. In the present invention, the mark detecting unit 12 in FIG. 12 is replaced by a matching processing unit 13. Therein, in calculating a displacement of machining position in the nth time (where, n=1, 2, 3, . . . ), the position displacement of the image is obtained from matching processing of the image data of D[n−1] in the (n−1)th time and the image data of D[n] at present (the nth time) to calculate a displacement of machining position. The position displacement of the mark image calculated by the matching processing unit 13 is input to the machining position correcting unit 11. The computer unit 7 instructs the ion beam control unit 5 based on an output from the machining position correcting unit 11 to correct a machining position of the focused ion beam by driving the ion bean control system 2 to adjust an irradiation position of the ion beam.

Figure 3:
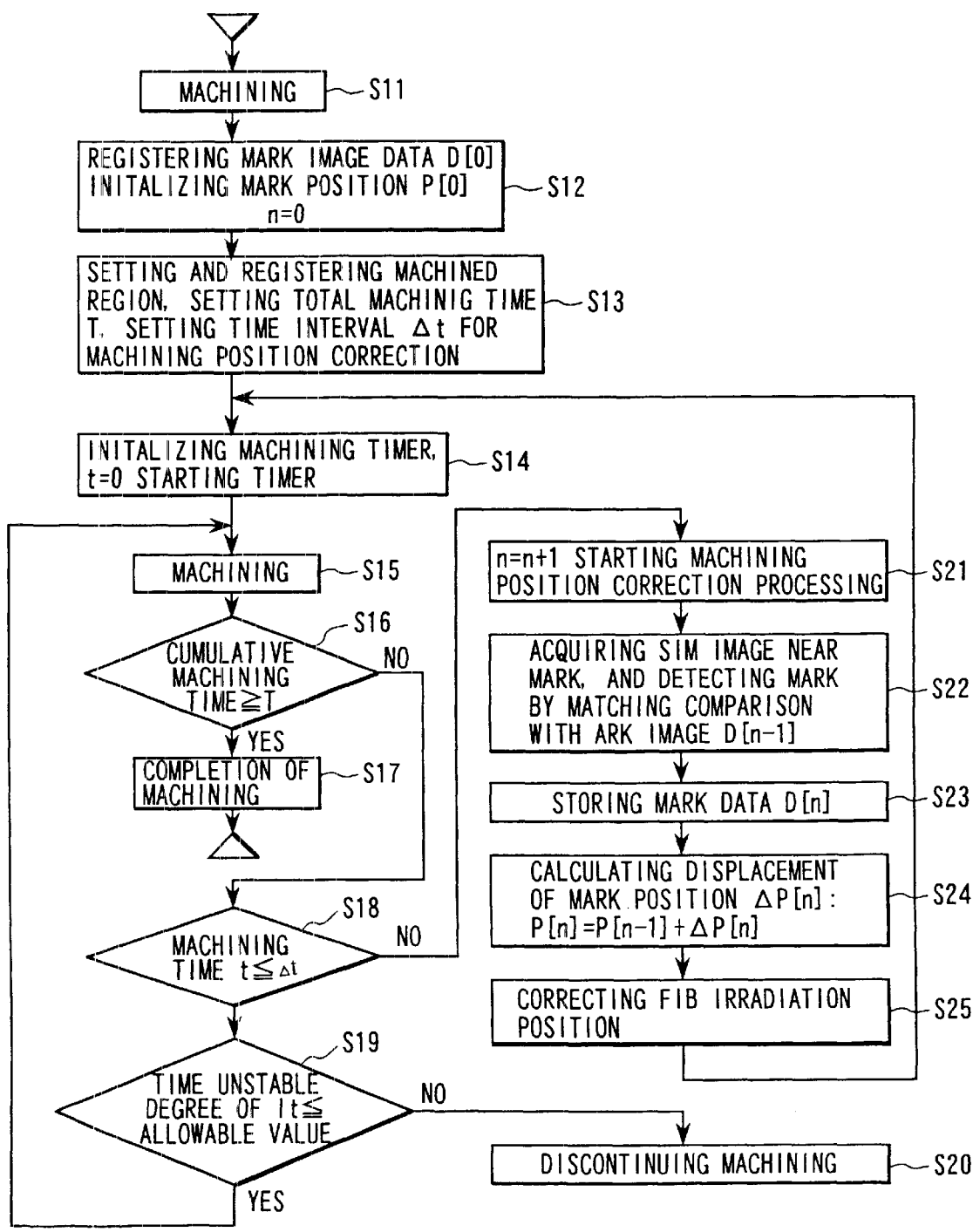
FIG. 3 is a chart showing an embodiment of a machining flow of an FIB machining method in accordance with the present invention.
Figure 4:
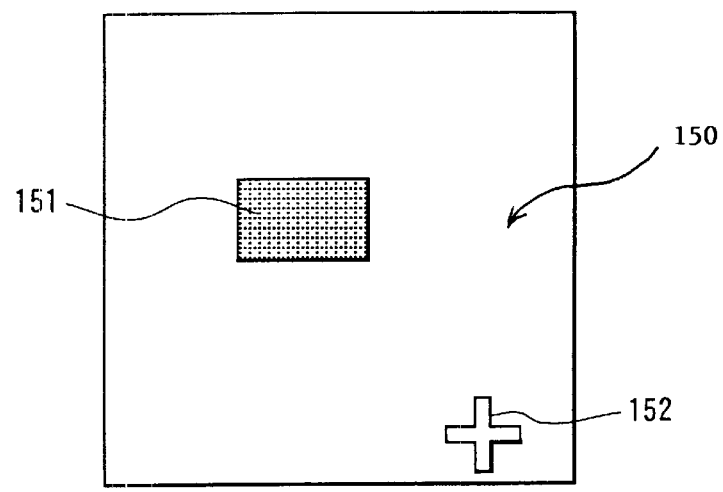
FIG. 4 is a view showing an example of machining by the FIB machining method in accordance with the present invention.
Figure 6A:
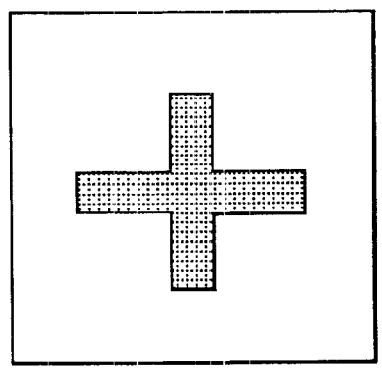
FIG. 6A to FIG. 6D are views showing SIM images exhibiting a history of sputter damage of a cross-shaped mark.
Figure 6B:
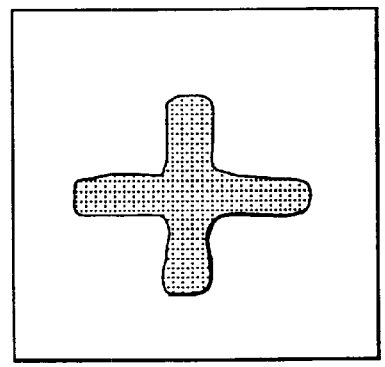
Figure 6C:
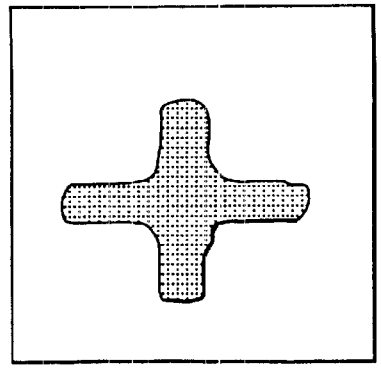
Figure 6D:
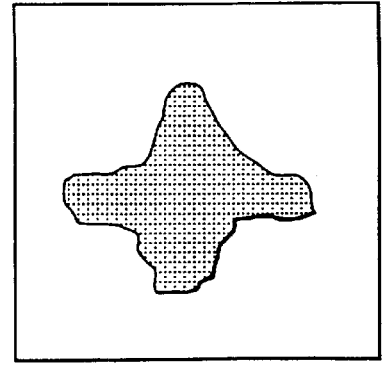

An FIB machining method in accordance with the present invention will be described below, referring to FIG. 3 and FIG. 4. FIG. 3 is a chart showing an embodiment of a machining flow of an FIB machining method in accordance with the present invention, and FIG. 4 is a view showing an example of machining by the FIB machining method in accordance with the present invention. The flow of machining after setting a sample just below the beam of the FIB apparatus is as follows. In the embodiment to be described here, a machined region on the sample 108 is a rectangular region 151 shown in FIG. 4. A mark 152 for detecting a displacement of beam irradiation position is a cross-shaped mark 152 of 5 μm×5 μm size, and is located outside the machined region 151.

① Machining of Registered Mark (S11)

The mark 152 for correcting a beam irradiation position is set and formed near the machined region 151. Therein, both the machined region 151 and the register mark 152 need to be located within a region 150 which can be covered only by FIB deflection using the deflector 105 without moving the sample stage 109.

② Registering of Mark Image Data D[0], and Initializing a Mark Position P[0] and n(S12)

Image data of the mark 152 and a mark position are registered using an SIM image displayed in the CRT. The registered image data becomes a reference mark image data D[0] of n=0 of the reference mark image data D[n−1] for correcting a beam irradiation position in the nth time. Similarly, initial data P[0] of two-dimensional (x, y) data P[n] of the mark position is initialized The two-dimensional (x, y) data P[n] is always expressed by taking the mark position of the SIM image acquired in prior to starting the machining as the origin.

③ Setting and Registering of Machined Region (S13)

The machined region 151 is set and a position of the machined region is registered. In addition, a total machining time T and a time interval Δt are also set.

④ Initializing (t=0) and Starting of a Machining Position Correcting Timer (S14)

⑤ Machining (S15)

Machining is continued until a cumulative machining time [=(n−1)Δt+t] reaches the total machining time T set in Step 17. When the cumulative machining time reaches the total machining time T, the processing proceeds from Step 16 to Step 17 to complete the machining.

⑥ Discontinuing of Machining and Machining Position Correcting Control Processing (S16 to S25)

If it is judged that the cumulative machining time has not reached the total machining time T, the processing proceeds to Step 18. If it is judged that the timer time t of the machining position correcting timer does not exceed Δt set in Step 13, the processing proceeds to Step 19. If it is judged in Step 19 that a time unstable degree of the ion current It emitted from the ion source and monitored during machining does not exceed a preset allowable value, the processing is returned to Step 15 to continue the machining. On the other hand, if the time unstable degree of the ion current It exceeds the allowable value, the processing proceeds from Step 19 to Step 20 to immediately discontinue the machining and display a message of "It unstableness" on the CRT.

If the timer time t of the machining position correcting timer exceeds Δt, the processing proceeds from Step 18 to Step 21 to increase n by n=n+1 and to start the machining position correction control processing in the nth time. When the machining position correction control processing is started, the machining is discontinued, and the processing proceeds to Step 22 to acquire an SIM image by scanning the focused ion beam on an area near the registered mark 152 for correcting the beam irradiation position. Then, a mark is detected through matching processing between the SIM image data and the reference mark image data D[n−1]. Next, the processing proceeds to Step 23 to store the detected image data of the mark D[n]. Successively, in Step 24, a position displacement ΔP[n] of the mark is calculated. The position displacement ΔP[n] of the mark expressed by always taking the mark position of the SIM image acquired prior to starting of the machining as the origin can be expressed by Equation (1) described below.

$$P[n]=P[n-1]+\Delta P[n]=\Delta P[1]+\Delta P[2]+\Delta P[3]+\ldots +\Delta P[n],$$

where $\Delta P[1]=P[0]+P[1]$, $\Delta P[2]=P[1]+P[2]$ \hfill (1)

Then, in Step 25, the FIB irradiation position is updated based on the mark position data P[n], and the processing is returned to Step 14 (the item (④ described above).

FIG. 5 is a functional block diagram of the image control unit 9 and the matching processing unit 13 of FIG. 2 for processing Step 22. The image control unit 9 comprises an image acquiring means 32 for acquiring the SIM image based on an output signal of the charged particle detector 107; a reference image updating means 34; an image memory 33 for storing a present image acquired by the image acquiring means 32; an image memory 35 for storing the reference image; and a detected mark image memory means (an image memory) 37 for storing the mark image D[n] detected by the matching processing unit 13. The image acquiring means 32 acquires the SIM image by receiving a timing signal from an image acquiring timing control means 31 comprising part of the computer unit 7. The matching processing unit 13 performs detection of the mark 152 and calculation of the position displacement of the mark image through matching between the present image A stored in the memory 33 and the reference image B stored in the memory 35. The position displacement of the mark image calculated in the matching processing unit 13 is input to the matching position correction unit 11. The computer unit 7 instructs the ion beam control unit 5 based on an output from the machining position correcting unit 11 to correct the machining position of the focused ion beam by driving the ion beam control system 2 to adjust an irradiation position of the ion beam.

When machining position correcting control processing in the nth time is started, the image acquiring timing control means 31 of the computer unit 7 transmits a timing signal to the image acquiring means 32 of the image control unit 9. By receiving the timing signal the image acquiring means 32 acquires an SIM image near the mark, and the acquired SIM image is stored in the image memory 33. This image is set as the present image A. On the other hand, the timing signal is also transmitted to the reference image updating means 34, and the reference image updating means 34 upon receipt of the timing signal acquires the detected mark image D[n−1] detected in the preceding time from the detected mark image memory means 37 to update the reference image B stored in the memory 35 to the mark image D[n−1] detected in the (n−1)th time.

Next, the matching processing unit 13 compares the present image A with the reference image B including the mark, and detects the mark in the present image A to calculate a position displacement ΔP[n] of the mark. Then, the detected image of the mark is stored in the detected mark memory means (the image memory) 37 as a detected mark image D[n]. The machining position correcting unit 11 calculates a beam irradiation position correcting value based on the mark position P[n] output from the matching processing unit 13. Machining is then continued using this beam irradiation position correcting value until the next machining position correcting control processing, that is, until the machining position correcting control processing in the (n+1)th time is started.

A key-point of the present embodiment is that when the reference image B of the mark is compared with the present image A, the whole reference image B is updated. In the conventional method, the reference image is not updated and the initial mark image D[0] always used as the reference image.

FIG. 6A to FIG. 6D are SIM images expressing a history of sputter damage of a cross-shaped mark, and show the typical SIM images D[n] of a cross shape for n=0, 20, 40, 60 in the present embodiment. It can be understood that the shape of the cross mark is damaged by sputtering and gradually changed from its original shape as n increases. However, according to the method of the present invention, even if the similarity between the image D[n] at the present time and the initial image D[0] is decreased, the mark can be detected as far as the similarity between the image D[n] at the present time and the image D[n−1] just before is maintained In the conventional method, the mark of, for example, n=60 is not recognized as a cross shape any longer, and accordingly the mark can not be detected from a comparative reference between the image D[60] at the present time and the mark reference image D[0].

A detailed example of the image matching processing used in the above-mentioned mark detection will be described below. Editing of the mark image before machining was performed by acquiring the SIM image containing the mark and then displaying the stored image on the CRT. A rectangle was drawn by dragging a mouse cursor on the screen, and the image inside the rectangular area was stored as the reference image. Editing of the position and the size of the rectangle can be performed by picking sides and corners of the rectangle and dragging it using the mouse. An image which is obtained by image processing (binary cording, noise removing, frame extracting and so on) of an original image of a mark may be registered as the reference image.

The mark image detected from the SIM image during machining is expressed by brightness in a binary representation and a two-dimensional array (that is, position) though the image processing. In addition, small black points and white points are deleted in order to extract characteristics of the image. The position displacement is calculated by superposing the reference image B on the present image A obtained in such a manner, and obtaining a position where the both images most agree with each other, that is, a position where an image correlation coefficient between the both images became largest. This method of comparing images is long in processing time, but high in accuracy of calculating the position displacement. It is very effective, in order to shorten the processing time, to convert the images to images having reduced data volume for the image (that is, sketched images) and then comparing them. However, the accuracy of calculating the position displacement is slightly decreased. In the present embodiment, the matching processing has been performed by taking the mark image in a nearly full area of the SIM image frame of 512×512 pixels, and converting it to a sketched image of 128×128 pixels.

Although the FIB machined cross-shaped mark 102 of 5 μm×5 μm may be employed as the mark in this embodiment, an extraneous substance may be employed as the registered mark if it has a "distinctive" sample pattern. The meaning of "distinctive" here is that there exists only one shape of the registered sample pattern in the acquired image, and the pattern shape will not be suddenly changed by the FIB machining, and, thus, its continuity will be maintained.

The registered mark is located outside the machined region 151 in this embodiment. However, if the registered mark is located inside the machined region, the mark can be used for another purpose other than the correction of beam irradiating position. That is, even if the sample pattern registered as a mark in a machined region varies in its shape and its position on the horizontal plane in the depth direction, the sample can be etched down by tracing the registered pattern in the machined region. After completion of the machining, a three-dimensional structure of the mark can be obtained by placing the mark images D[n] at their-respective depths and shifting the mark images by the image position displacements α P[n] which have been displaced to trace the mark image.

Figure 7A:
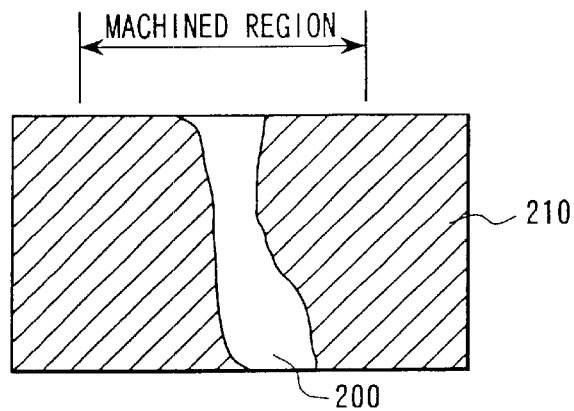
FIG. 7A to FIG. 7C are cross-sectional views showing a machined sample having a structural body used as a registered mark in a machined region, where both of size and planar position of the structural body are continuously changed in the depth direction.
Figure 7B:
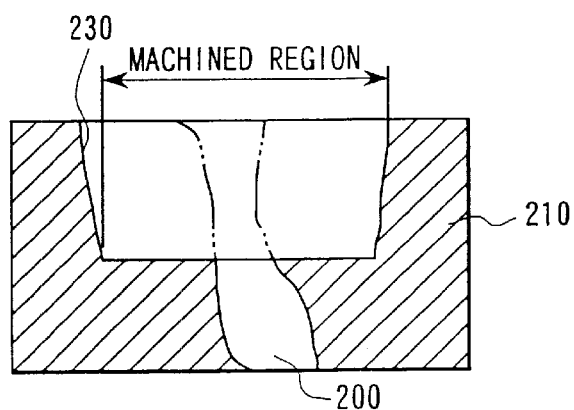
Figure 7C:
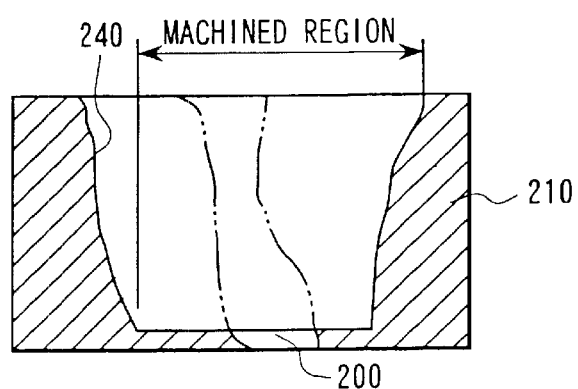

Another embodiment will be described below, referring to FIG. 7A to FIG. 7C. FIG. 7A to FIG. 7C are schematic views showing cross sections of a machined sample having a structural body used as a registered mark in a machined region, and both of size and planar position of the structural body are continuously changed in the depth direction. FIG. 7A shows a state before machining, and FIG. 7B and FIG. 7C show state as the machining progresses.

The sample 210 had a structural body 200. Both the size and the planar position of the structural body continuously changes in the depth direction. The shape the structural body exposed on the sample surface was used as a registered mark. Similar to the case of the above-mentioned embodiment, the method of calculating the position displacement of the mark is that an SIM image of the machined region is acquired at a preset time intervals, and the mark image D[n] is detected through matching processing between the SIM image and the mark image (the exposed shape of the structural body 200) D[n−1] detected in the time just before.

In this embodiment, the position of the machined region is moved in synchronism with change of the planar position of the structural body 200 without changing the size of the machined region even if the planar position of the structural body 200 is changed. Therefore, the machined side walls 230, 240 are not flat, as shown in FIG. 7B and FIG. 7C. Such a machining method is effective in a case where machining is performed by tracing the structural body 200 even if information on the shape and position of the structural body 200 inside the sample is not known. This method is characterized in that, if the planar position of the structural body 200 almost falls within an initially set machined region in the inside of the sample, machining can be performed by tracing the structural body. In the conventional machining method of etching down in fixing the size and the position of the machined region, the planar position of the structural body must fall within an initially set machined region in the inside of the sample. In the present embodiment, in the vicinity of a frame of the SIM image obtained from the machined region of a scanned region, an image of a machined side wall which has been formed appears and disappears in the vicinity of the frame of the image. Therefore, it is preferable that the image only in the central portion which is not affected by the above-mentioned effect is employed as the mark image data D[n] for registering.

In the above-mentioned embodiments, the total machining set time T is a fixed time period set before starting of the machining. However, it is possible to employ, for example, a time point when a time change curve of an intensity of a machining monitor signal (secondary electrons, secondary ions or the like) satisfies a specified condition, that is, a time point which can not be determined until the machining is actually performed because a desired machined depth is not accurate.

Figure 8A:
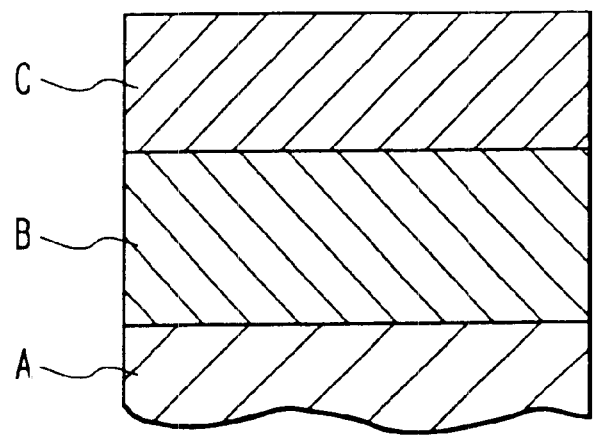
FIG. 8A and FIG. 8B are explanatory views showing an example of determining a total machining time based on a machining monitor signal during machining.
Figure 8B:
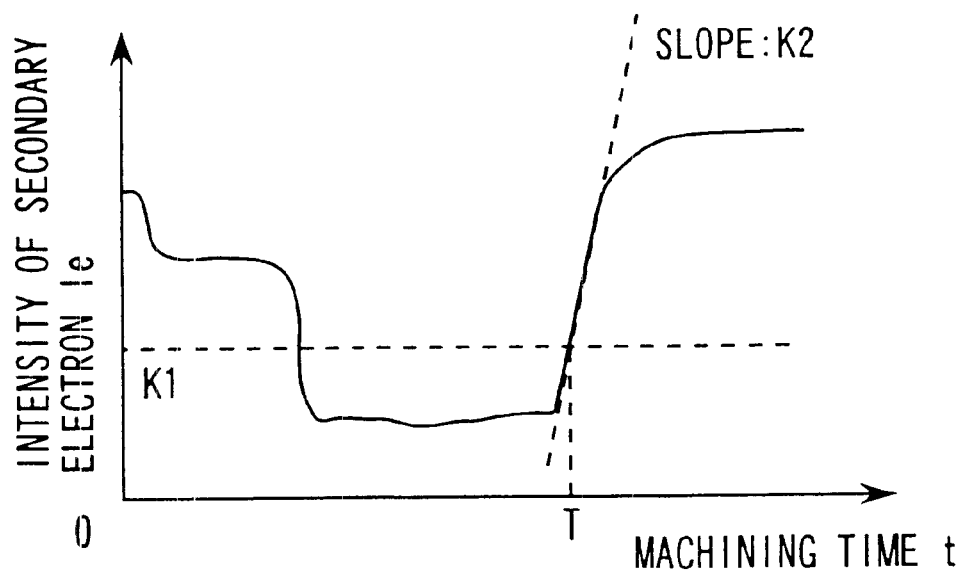

FIG. 8A and FIG. 8B are explanatory views showing an example of determining a total machining time based on a machining monitor signal obtained during machining. FIG. 8A is a schematic view of a cross-sectional structure of a sample to be machined and FIG. 8B is a graph showing a time change of an intensity of a secondary machining monitor signal (secondary electrons). The sample is formed by laminating two layers of films B and C on a substrate A. The target machining depth in this case is assumed to be a position of an interface between the substrate A and the film B.

Yields of secondary electrons of a 30 keV-Ga ion beam to the material A, B and C decrease in order of C, A, B, and the time change of intensity of the secondary electrons Ie(t) becomes as shown in FIG. 8B. Therefore, two specified conditions for determining termination of machining were set, that is, ① an intensity of the secondary electrons Ie is to be higher, than a set value K1, and ② a slope of the curve (ΔIe/Δt) of the secondary electrons Ie to machining time is to be larger than a set value K2. Time T in FIG. 8B corresponds to a time period that satisfies the both conditions. The Ie curve after the time T shows an estimated curve which would occure if the machining were not completed at the time T.

Figure 9:
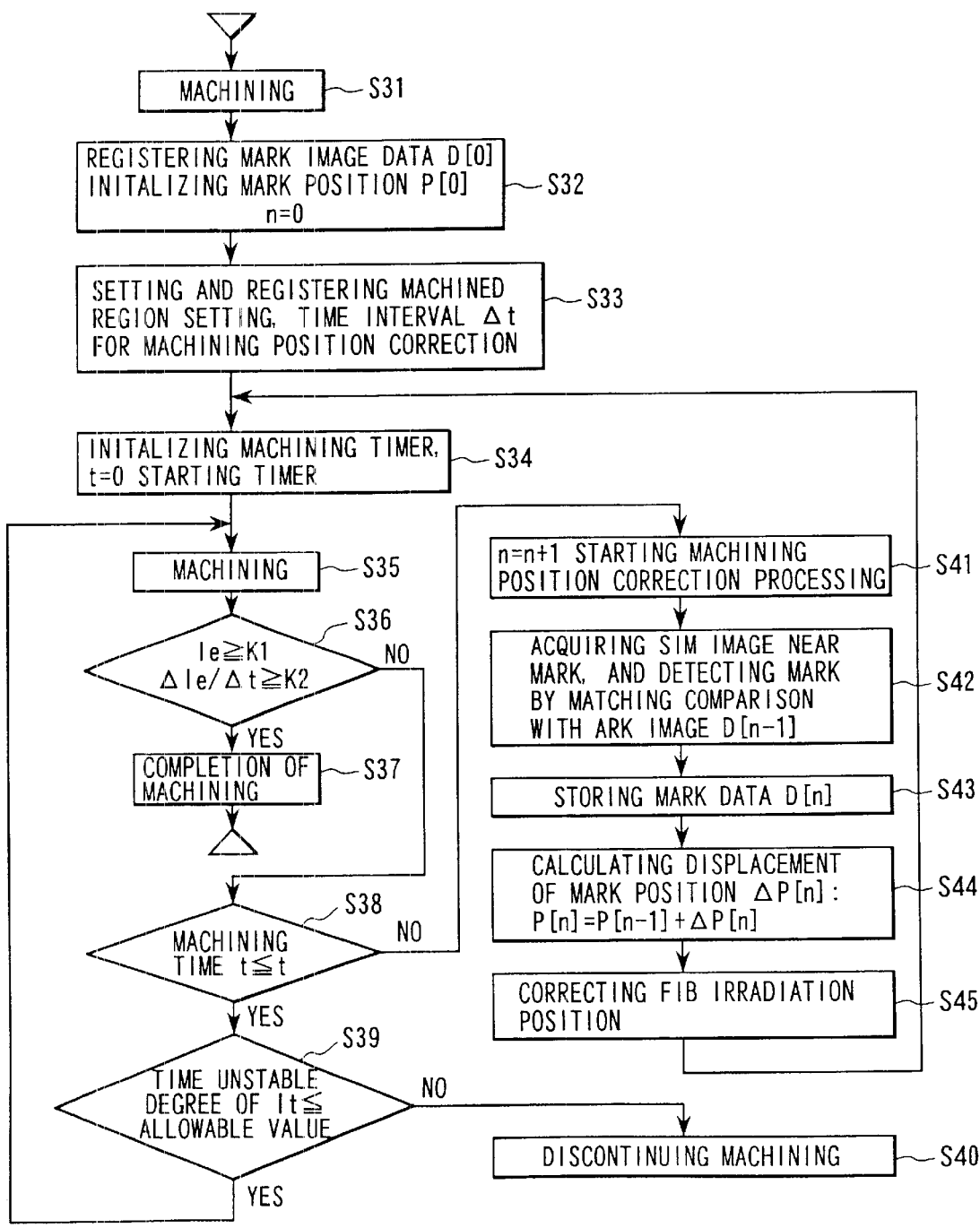
FIG. 9 is a chart showing another embodiment of a machining flow of an FIB machining method in accordance with the present invention.

FIG. 9 is a chart showing the machining flow in this case. The machining flow chart of FIG. 9 corresponds to the machining flow chart of FIG. 3 in which the judging condition of the machining time in Step 16 is changed to Ie≧K1, ΔIe/Δt≧K2.

In the flow chart of FIG. 3 or the flow chart of FIG. 9, a time interval Δt for acquiring the SIM image of a sample for correcting the machining position is set in Step 13 or Step 33. In this example, the time interval Δt is constant. However, the time interval Δt may be variable.

Variation of the time interval Δt may be performed as follows. When a displacement of the mark position ΔP[n] calculated in Step 24 of FIG. 3 or in Step 44 of FIG. 9 is larger than a preset displacement ΔP1, a value (Δt−ti) obtained by subtracting a preset time t1 from Δt is newly reset as the time interval Δt in Step 24 or Step 44 after calculating the mark position P[n], to increase correction frequency of the FIB irradiation position. On the contrary, when a displacement of the mark position ΔP[n] calculated in Step 24 of FIG. 3 or in Step 44 of FIG. 9 is smaller than a preset displacement ΔP2, a value (Δt+t2) obtained by adding a preset time t2 (it is possible that t2=t1) to Δt is newly reset as the time interval Δt in Step 24 or Step 44 after calculating the mark position P[n], to decrease correction frequency of the FIB irradiation position. By decreasing the correction frequency, damage of the sample can be reduced and damage of the mark can be also decreased.

Another embodiment of the present invention will be described below, referring to FIG. 10A and FIG. 10B. The present embodiment relates to forming a section of an extraneous substance in a micro-device, and is capable of automatically determining a termination of machining. FIG. 10A and FIG. 10B are views explaining a method capable of automatically determining a termination of machining. FIG 10A is a schematic cross-sectional view of a sample, and shows the cross-sectional structure of the sample containing the extraneous substance buried therein and machined bottom positions at time t1, t2, . . . , t6 during machining. FIG. 10B shows SIM images of the machined region at the time t1, t2, . . . , t6. In this case, correction of the FIB irradiation position can be performed using a registered mark set outside the machined region, as in the above-mentioned embodiment. Since the key point is only to determine a termination of machining, correction of FIB irradiation position may be omitted if the requirement placed on the accuracy of the FIB irradiation position is loose.

The sample 310 contains the extraneous substance 300 as schematically shown the cross section in FIG. 10A, and the target machining depth is a depth which is over-etched slightly beyond the bottom of the extraneous substance 300 in the machined section. The time t1 is the starting time of machining, and a pattern 300a of the extraneous substance 300 appears in the SIM image acquired at that time. As time elapses and the machining progresses, slightly different patterns 300b, 300c, 300d of the extraneous substance reflecting the three-dimensional shape of the extraneous substance appear in the SIM image of the machined region. The structural pattern disappears from the SNM image just at time t5. Termination of the machining is at the time t6, a time Δt after time t5 when the structural pattern disappears from the SIM image elapsing for the desired over-etching. Since the machining termination condition was determined as the time of adding time Δt to the time of disappearance of the structural pattern, the total machining time T was determined by t6 (=t5+Δt).

Figure 11:
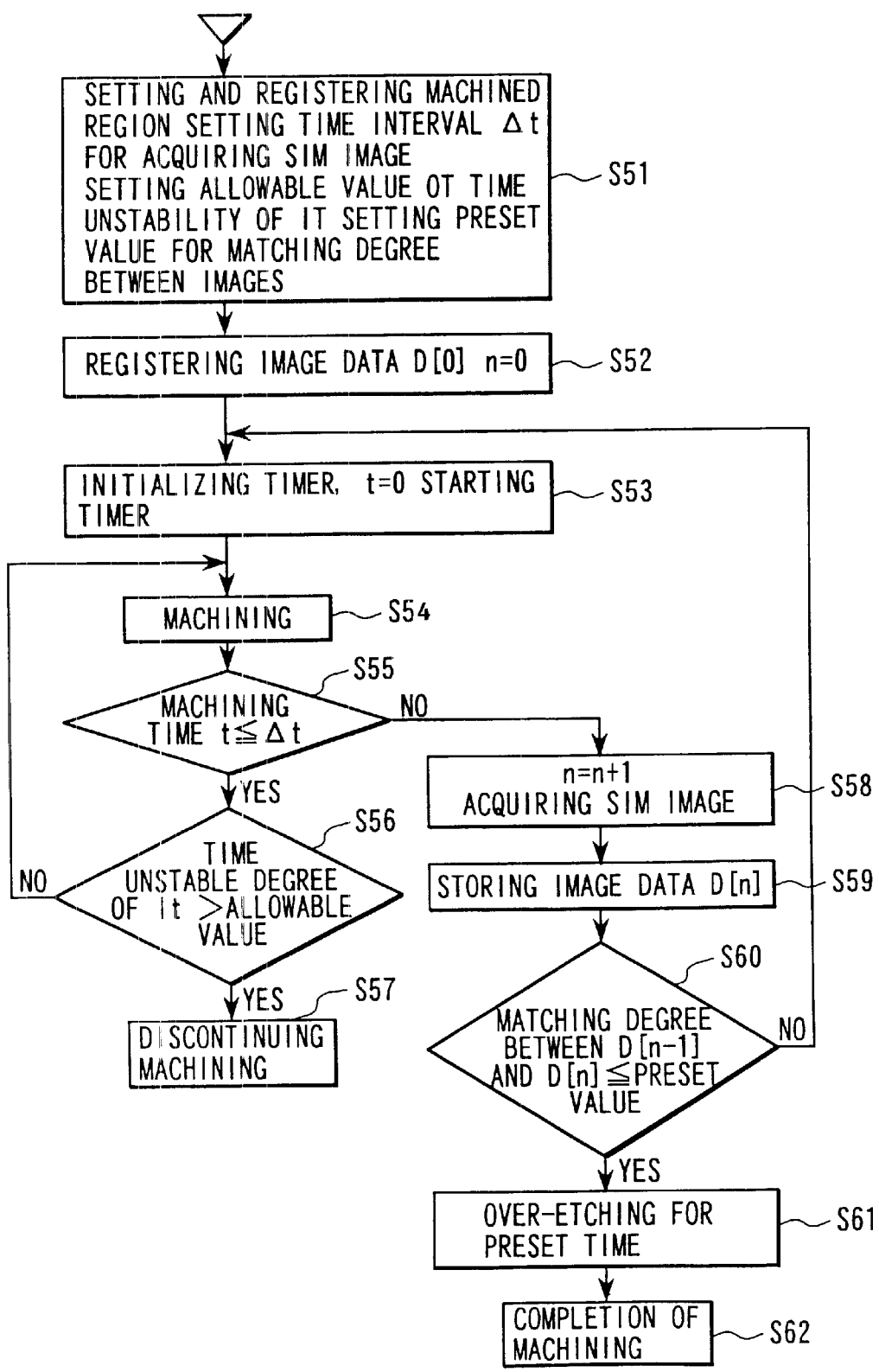
FIG. 11 is a chart showing an example of a machining flow of an FIB machining method which automatically detects termination of machining.

FIG. 11 is a chart showing an example of a machining flow of an FIB machining method which automatically detects termination of machining. The example is a flow in which correction of the FIB irradiation position is omitted. Initially, in Step 51, a machined region is set and registered, a time interval Δt for acquiring a SIM image is set, and an allowable value for time unstableness of It and a set value for a matching degree between images are set. Next, in Step 52, image data D[0] used for detecting a termination of machining in the SIM image of the machined region is registered. In the example shown in FIG. 10, the extraneous substance pattern 300a in the SIM image acquired at time t1 corresponds to D[0]. Next, in Step 53, a timer is initialized and started. Successively, the processing proceeds to Step 54 to start machining. In Step 55, machining time is monitored. If the machining time t measured by the timer is below Δt, the processing proceeds to Step 56. In Step 56, if it is judged that the degree of time unstableness of an ion current It emitted from the ion source does not exceed the preset allowable value, the processing is returned to Step 54 to continue the machining. If the degree of time unstableness of an ion current it emitted from the ion source exceeds the preset allowable value, the processing proceeds from Step 56 to Step 57 to discontinue the machining and to display a massage of "It is unstable" on the CRT.

On the other hand, if the machining time t measured by the timer exceeds Δt, the processing proceeds from Step 55 to Step 58 to increase n and acquire the SIM image of the machined region. The image data in the SIM image is stored in D[n] in Step 59. Then, the processing proceeds to Step 60 to compare the image data D[n] acquired this time with the image data D[n−1] acquired the president time. As the result of the comparison, if the matching degree between the both images exceeds a preset value, the processing is returned from Step 60 to Step 53 to continue the machining. On the other hand, if it is judged in the judgment in Step 60 that the matching degree between the both images decreased below the preset value, the processing proceeds to Step 61 to perform over-etching for a preset time. Then, the processing proceeds to Step 62 to terminate the FIB machining. Therein, a matching correlation coefficient between the both image is used for the matching degree of the both images.

In a case of detecting termination of machining while the FIB irradiation position is being corrected, for example, the processing corresponding to Step 42 to Step 45 of FIG. 9 may be performed on the way returning from the judgment in Step 60 to Step 53 in the flowchart shown in FIG. 11.

The present invention can be carried out using an FIB machining apparatus, in which the matching processing unit 13 in the functional block diagram shown in FIG. 5 is replaced by a comparing processing unit for comparing two SIM images, or using an FIB machining apparatus assigns a function of comparative processing to the matching processing unit 13. However, the image to be used for comparative processing is not a machined registered mark for correcting the beam irradiation position, but an image of a distinctive pattern in the SIM image of the machined region.

Description has been made here of an example in which judgment of machining termination is performed by detecting that the structural pattern D[n−1] existing in the SIM image acquired in the (n−1)th time disappears in the SIM image acquired in the following time, that is, the nth time. However, the judging criterion for the termination of machining is not limited to disappearance of a pattern. In a case, for example, of a sample in which a pattern (for example, ○ or □) that did not exist before appears when the sample is machined down to a desired depth, appearance of the pattern (for example, ○ or □) may be employed as ajudging criterion of machining termination. In a case where a shape of a pattern existing on a machined surface suddenly changes when the sample is machined to a desired depth, the sudden change in the pattern, that is, a sudden change in the matching degree between the images may be employed as a judging criterion of machining termination.

In the above-mentioned two embodiments, it is difficult to accurately estimate the total machining time T in advance because the sample structure is unknown, or knowledge on the sample structure is inaccurate, and because the machining rate depends on the machining conditions such as the kind of the material, the machining area, the FIB current and the scanning speed. However, according to the present invention, since the target machining depth can be optimally determined while the sample is actually being machined, the machining can be efficiently performed. This effect is directed to high efficiency of the machining, and belongs to a different sphere from the high accuracy of the machining position.

According to the present invention, it is possible to correct a displacement of machining position even if the registered mark is damaged by an ion sputtering phenomenon and the shape of the mark is largely changed from an initial shape of the mark. Further, it is possible to optimally determine a machining termination of an FIB machining.

What is claimed is:

1. A method of machining a sample using a focused ion beam, comprising:
   acquiring a scanning ion microscopic image of the sample at each of a plurality of preset time intervals;
   upon each acquisition, updating reference image data D[n−1] in a specified region inside a scanning ion microscopic image with image data acquired at the previous time (n−1) and updating present image data D[n] in the specified region inside a scanning ion microscopic image with image data acquired in a present time (n), where n=1, 2 3, . . . ;
   calculating a position displacement of the image based on the reference image data D[n−1] and present image data D[n]; and
   correcting a machining position by displacing an irradiation position of the focused ion beam by the calculated position displacement.

2. A method according to claim 1, wherein said specified region inside the scanning ion microscopic image is a region located outside a machined region and including a distinctive pattern.

3. A method according to claim 2, wherein said distinctive pattern located outside the machined region is a mark pattern formed in prior to starting of machining.

4. A method according to claim 1, wherein said specified region inside the scanning ion microscopic image is a region located inside a machined region and including a distinctive pattern.

5. A method according to claim 1, wherein the time interval between acquiring the scanning ion microscopic images is shortened when said position displacement of the image is larger than a first set value, and the time interval between acquiring the scanning ion microscopic images is lengthened when said position displacement of the image is smaller than a second set value.

6. A method of machining a sample using a focused ion beam, comprising:
   acquiring a scanning ion microscopic image of a region containing a distinctive pattern located inside a machining region of the sample at preset time intervals;

detecting a shape change of the pattern based on image data D[n−1] in a specified region inside a scanning ion microscopic image in the (n−1)th time and image data D[n] in the specified region inside a scanning ion microscopic image in the nth time acquired in the above step, where n=1, 2, 3, . . . ; and judging a termination of machining based on said shape change of the pattern.

7. A focused ion beam machining apparatus comprising:

an ion source;

an ion beam control system for accelerating, focusing and deflecting an ion beam emitted from said ion source;

a secondary particle detector for detecting secondary particles emitted from a sample by irradiating the ion beam onto the sample;

an image control unit for acquiring a scanning ion microscopic image of the sample at each of a plurality of preset time intervals based on an output of said secondary particle detector;

a matching processing unit for, upon each acquisition, updating reference image data D[n−1] in a specified region inside a scanning ion microscopic image with image data acquired at the previous time (n−1) and updating present image data D[n] in the specified region inside a scanning ion microscopic image with image data acquired in a present time (n), where n=1, 2 3, . . . , and calculating a position displacement of the image from matching processing of the reference image data D[n−1] and the present image data D[n]; and a control unit for controlling said ion beam control system so as to compensate the position displacement of the image calculated by said matching processing unit.

8. A focused ion beam machining apparatus comprising:

an ion source;

an ion beam control system for accelerating, focusing and deflecting an ion beam emitted from said ion source;

a secondary particle detector for detecting secondary particles emitted from a sample by irradiating the ion beam onto the sample;

an image control unit for acquiring a scanning ion microscopic image of the sample at preset time intervals based on an output of said secondary particle detector; and an image comparing unit form comparing image data D[n−1] in a specified region inside a scanning ion microscopic image in the (n−1)th time and image data D[n] in the specified region inside a scanning ion microscopic image in the nth time acquired by said image control unit, where n=1, 2, 3, . . . , wherein machining is terminated when a degree of matching between the two kinds of image data compared by said image comparing unit exceeds a predetermined value.

* * * * *

UNITED STATES PATENT AND TRADEMARK OFFICE
CERTIFICATE OF CORRECTION

PATENT NO. : 6,521,890 B2
DATED : February 18, 2003
INVENTOR(S) : Tohru Ishitani et al.

It is certified that error appears in the above-identified patent and that said Letters Patent is hereby corrected as shown below:

Column 1,
Line 12, change "of the samples" to -- of samples --.
Line 16, delete "position".

Column 2,
Line 38, change "SIN" to -- SIM --.

Column 8,
Line 58, change "α Pn" to -- Δ Pn --.

Column 12,
Line 2, change "ajudging criterion" to -- a judging criterion --.

Signed and Sealed this

Sixth Day of July, 2004

JON W. DUDAS
*Acting Director of the United States Patent and Trademark Office*